United States Patent
O'Halloran

(10) Patent No.: US 7,169,148 B2
(45) Date of Patent: Jan. 30, 2007

(54) BEVELED TONSIL SUCTION CAUTERY DISSECTOR

(76) Inventor: Laurence R. O'Halloran, 4703 N. 16th St., Arlington, VA (US) 22207

( * ) Notice: Subject to any disclaimer, the term of this patent is extended or adjusted under 35 U.S.C. 154(b) by 340 days.

(21) Appl. No.: 10/655,555

(22) Filed: Sep. 5, 2003

(65) Prior Publication Data

US 2004/0082951 A1    Apr. 29, 2004

Related U.S. Application Data

(60) Provisional application No. 60/409,199, filed on Sep. 10, 2002.

(51) Int. Cl.
*A61B 18/18* (2006.01)

(52) U.S. Cl. ........................................ 606/49

(58) Field of Classification Search .................. 606/41, 606/45–50; 604/35
See application file for complete search history.

(56) References Cited

U.S. PATENT DOCUMENTS

| | | | |
|---|---|---|---|
| 3,828,780 A * | 8/1974 | Morrison, Jr. ............... | 604/20 |
| 3,974,833 A | 8/1976 | Durden, III | |
| 4,411,266 A * | 10/1983 | Cosman ........................ | 606/49 |
| 4,548,207 A * | 10/1985 | Reimels ....................... | 606/50 |
| 5,084,045 A | 1/1992 | Helenowski | |
| 5,180,363 A | 1/1993 | Idemoto et al. | |
| 5,314,406 A | 5/1994 | Arias et al. | |
| 5,441,503 A * | 8/1995 | Considine et al. .......... | 606/115 |
| 5,520,685 A | 5/1996 | Wojciechowicz | |
| 5,599,345 A * | 2/1997 | Edwards et al. ............... | 606/41 |
| 5,730,742 A * | 3/1998 | Wojciechowicz ............ | 606/49 |
| 5,800,431 A | 9/1998 | Brown | |
| 5,904,681 A | 5/1999 | West, Jr. | |
| 5,922,003 A | 7/1999 | Anctil et al. | |
| 5,925,045 A * | 7/1999 | Reimels et al. ............... | 606/48 |
| 5,980,518 A | 11/1999 | Carr et al. | |
| 6,042,538 A | 3/2000 | Puskas | |
| 6,669,695 B2 | 12/2003 | Luigi | |

* cited by examiner

*Primary Examiner*—Michael Peffley
(74) *Attorney, Agent, or Firm*—Hunton & Williams LLP

(57) ABSTRACT

A suction cautery dissector comprising a handle assembly, a tubing assembly having a suction channel formed therein, the tubing assembly comprising a first portion connected to the handle assembly and a distal end, and a tip assembly at the distal end of the insulated tubing assembly, the tip assembly comprising a substantially co-planar, enclosed cautery surface with a beveled leading edge sharpened for dissecting tissue. The cautery surface provides an opening formed therein that communicates with the suction channel in the insulated tubing assembly and being operably connected to an electrical source. The tip assembly comprises a tip wall terminating at the cautery surface and wherein the tubing assembly comprises an insulating layer covering the suction channel from the first portion to the distal end, terminating at a minimum predetermined distance along the tip wall from the cautery surface around the circumference of the tip assembly to enable the tip assembly to make surface contact around the entire tip wall.

11 Claims, 5 Drawing Sheets

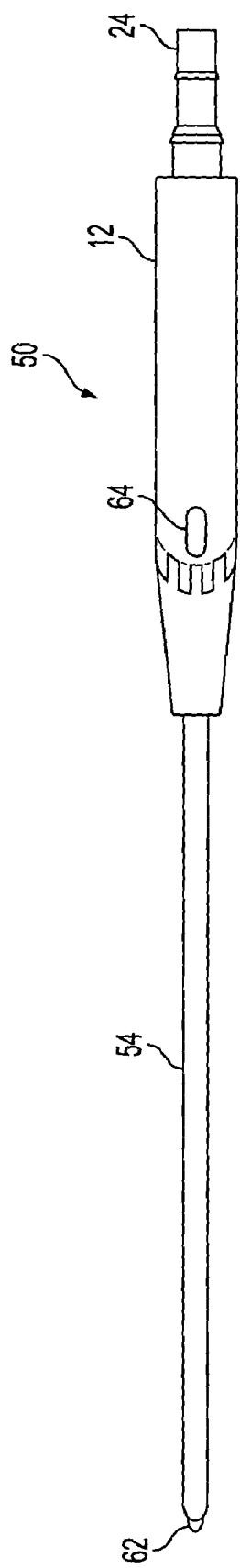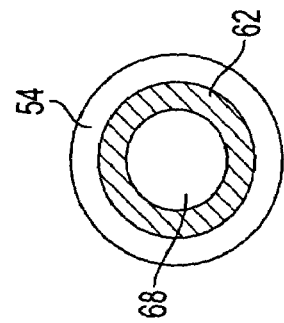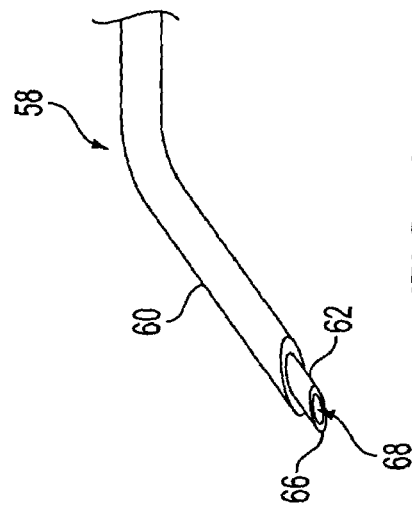
FIG. 3
FIG. 5
FIG. 4

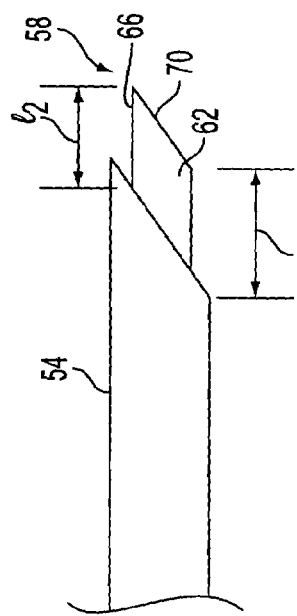
FIG. 7
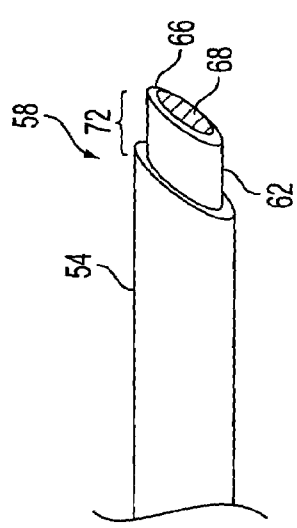
FIG. 9
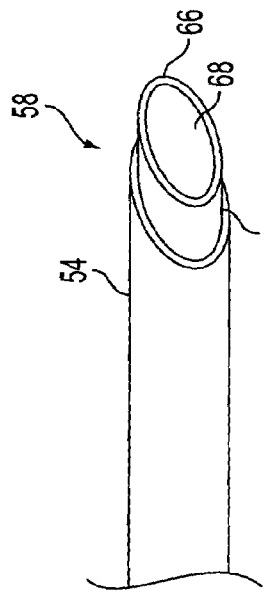
FIG. 10
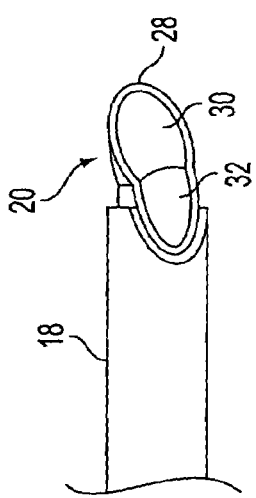
FIG. 6
PRIOR ART
FIG. 8
PRIOR ART

BEVELED TONSIL SUCTION CAUTERY DISSECTOR

RELATED APPLICATIONS

This application claims priority from U.S. Provisional Patent Application No. 60/409,199 filed on Sep. 10, 2002 entitled "Beveled tonsil suction cautery dissector."

FIELD OF THE INVENTION

The present invention relates to the field of surgical devices used for dissection of tissue in confined spaces.

BACKGROUND OF THE INVENTION

About Tonsillectomy

Tonsillectomy is one of the most commonly performed surgical procedures in the United States with approximately 400,000 operations conducted per year. The tonsils are masses of lymphoid tissue that are embedded in the lateral wall of the pharynx or throat. They are large in the younger years but progressively atrophy as the patient ages. Tonsillectomy is the surgical procedure performed typically under general anesthesia in which the tonsils are removed from the patient's throat in order to treat a disease state involving the tonsils.

Indications for Tonsillectomy

The two disease processes that most commonly affect the tonsils and provide the indications for tonsillectomy are chronic tonsillitis and tonsillar hypertrophy. Chronic tonsillitis occurs when bacteria is retained in or trapped by tonsillar tissue and this leads to chronic infection which eventually becomes unresponsive to medical therapy using antibiotics. When the frequency of infection becomes excessive, physical removal of the tonsillar reservoir of infection becomes necessary. Tonsillar hypertrophy or the development of excessively large tonsils leads to obstructive breathing problems and airway obstruction and is associated with sleep apnea. Tonsillectomy is most commonly performed in the pediatric population but is also performed on adults—most commonly for chronic tonsillitis.

Anatomy

The tonsils lie bilaterally on the lateral walls of the throat in a pocket created between two folds of the soft palate known as the anterior and posterior pillars of the tonsil. The soft palate consists of mucous membrane lining underneath, which is a layer of muscle. The tonsils themselves lie in this pocket and sit on a bed of muscle.

Tonsillectomy Procedure

The tonsillectomy procedure may be thought of in two stages. In the exposure stage, the tonsil is exposed by cutting through overlying mucous membrane and muscle tissue that conceals the tonsil. In the dissection stage, the tonsil itself is separated free from the underlying muscle bed and removed. In the first stage, the tonsil is grasped with a forceps and retracted towards the midline of the throat. A cut is made in the superior pole of the tonsil through the mucous membrane of the anterior tonsillar pillar. Next, the muscular layer below is divided until the proper tissue plane is reached. These mucous membrane and muscle cuts are made with a sharp instrument, such as a needle-tipped electrocautery unit. Next, dissection is carried inferiorly separating the tonsil tissue from the underlying muscle until the inferior pole of the tonsils is reached and transacted. This phase requires blunt dissection with a pushing motion as the tonsil may be "peeled" away from the underlying tissue. Identifying and staying within the confines of this dissection plane is crucial for a variety of reasons. First, maintenance of a proper plane of dissection minimizes injury to and tearing of the underlying muscular layer. This minimizes bleeding thereby reducing the need for electrocautery and thereby reducing post operative pain. During this stage, numerous perforating blood vessels are encounted which must be well-cauterized in order to avoid intra-operative and post-operative bleeding. Intra-operative bleeding obscures the surgical field and post-operatibe bleeding forces a return of the patient to the operating room for control of hemorrhage. Most commonly, two instruments are used to perform tonsillectomy. In the first or exposure stage a sharp needle-tipped electrocautery is used to expose the tonsil. In the second or dissection stage, a suction-electrocautery is used to control bleeding.

A variety of tools for tonsillectomy have been developed over the years including sharp instruments such as scalpels, electro-cautery units, lasers. The most commonly used tool is the electro-cautery unit.

The goals of an ideal tonsillectomy technique include the following: minimization of bleeding and minimization of post-operative pain and minimization of operative time. Minimization of bleeding during the procedure is important to improve visualization of the surgeon and to control patient blood loss especially in younger children. Minimization of post operative pain improves patient comfort and reduces the amount of time-off for both patients and caregiver parents of children. Dehydration is a common complication following tonsillectomy and is related to post operative pain on swallowing. Minimization of operative time maximizes efficient use of operating room time and reduce the amount of time patients are subjected to general anesthesia. It is well accepted that postoperative pain is minimized with minimal exposure of tissue to electrocautery. Therefore any technique that limits or reduces the amount of electrocautery applied can be expected to cause less post-operative pain.

An existing public domain device (PDD) is manufactured by A&E a New Jersey corporation that is owned by Alto Medical Corporation. One such PDD device is depicted in prior art FIGS. 1, 6, 8, 11, and 13. Specifically, a PDD suction coagulator 10 is shown. That device provides a handle assembly 12, a handle grip 14, and a cannula 16. The cannula 16 comprises an insulation layer 18 and a tip 20 at the distal end 22 of the cannula 16. In addition, the handle assembly 12 is provided with a suction port 24 and an electrical cord 26. This device operates by connecting a suction tube to suction port 24 and an electrical power to electrical cord 26. Electrical cord 26 connects through the handle assembly to a metal chamber inside cannula 16 that connects to cauterizing tip 20. Accordingly, tip 20 is used for dissection. In addition, suction may be applied through suction port 24 in an attempt to suck liquids or other materials at the dissection or cauterizing area.

As shown in FIG. 6, tip 20 may comprise a tab end 28 that terminates at a convex portion 30 which is connected to an intake portion 32. As FIGS. 6, 8, 11, and 13 illustrate, the PDD metal tip is designed for dissection but has many problems with respect to cauterizing and suction. Indeed, there are many problems with the PDD. First, with respect to tip shape and angulation, the PDD metal tip is a broad, round, long, widely curved and somewhat flimsy metal tab which makes blunt dissection unrewarding and is not pointed enough for precise dissection. The tip does not provide adequate current density to allow pinpoint cutting. The PDD tip is not well suited for blunt dissection.

In addition, the PDD provides electrical insulation on the main shaft that extends the full length of the tube. Only the metal "tab" sticking out conducts current. This tab prevents proper contact of tissue with the tube lumen thereby impairing effective cautery. This leaves very little exposed metal for conductive contact with the tissue. The insulation going down the full length of the tube prevents adequate contact with the tissue being sucked into the tube.

Also, the PDD device locates the suction port on the side of the unit towards the lumen of the tube. This is ergonomically incorrect for proper thumb positioning when performing the procedure.

Other drawbacks and disadvantages exist for existing surgical devices.

SUMMARY OF THE INVENTION

Various embodiments of the beveled suction cautery of the present invention provide an improvement and modification to the standard suction electro-cautery unit available from many suppliers. Modification and improvement of this device includes alteration to the design of the tip of the unit with a specific purpose of optimizing the performance of tonsillectomy and adenoidectomy.

In one embodiment, the beveled suction cautery dissector incorporates a malleable, insulated central metal tube connected to a plastic handle base. A standard suction tube attaches to the base as does the mono-polar electrical input cord. The plastic base has a finger suction port to regulate suction power. The central metal tube may comprise a composite of conductive metal coated with an outside layer of insulation except at the exposed tip. A hollow channel formed of an inner metal allows suction to pass through the tube to a suction port and out of the device for proper disposal. The central metal tube may be malleable, but in at least one embodiment, may be formed at a 40-degree angle bend (thus forming a 140 degree obtuse angle between the straight portion and the distal end of the metal tubing). The vertex of the angled portion or bend may be provided approximately 2 c.m. from the end of the tip. The location(s) and angle of this bend, however, may be modified and customized by the user depending on individual clinical circumstances. The actual metal tip itself may cut at a beveled angle, in its preferred embodiment at 45-degrees. Insulation may be provided on the central metal tube from the portion that enters the handle to a point on the distal end of the tubing that stops at a predetermined distance from the end. Preferably, this distance is at least between 2 mm and 0.5 cm, but other distances may also be used to expose the inner metal core for direct cautery.

Advantages of Various Embodiments of the Invention

Tonsillectomy is traditionally done with needle-tip electrocautery, suction-tip electrocautery or blunt dissection or a combination of the above. The embodiments of the present invention replace tools used in these three techniques with one device. In the embodiments of the invention, the functions of exposing the tonsil and controlling bleeding are combined into one unit. This provides cost benefits and operative time savings as the surgeon only needs to handle one instrument and avoids switching back and forth between two instruments.

The first stage or exposure stage is carried out with the sharp beveled tip of the unit. The sharp edge allows rapid cutting in a manner similar to traditional needle-tip electrocautery. In the dissection stage, blunt dissection is carried out with the beveled tip. In one embodiment, the leading edge may have an ovoid shape, thus providing an ideal pushing force for blunt dissection. Perforating blood vessels routinely encountered during this stage may be instantly cauterized with the beveled suction tip before bleeding obscures the field.

Sharp Tip Electrocautery

Sharp-tip electrocautery allows rapid and precise cutting of tissue by focusing energy in a small spot. One disadvantage in prior art systems has been the difficulty in controlling significant bleeding with the small tip. Frequently, a second suction coagulator device must be opened to achieve homeostasis. With the embodiments of the present invention, a sharp tip is incorporated into the tip but there is no need to switch to a second suction coagulator device with time savings for the surgeon and cost benefits for the facility.

Blunt Dissection

Blunt dissection that maintains a natural plane of dissection in a sub capsular plane has always been considered the "gold-standard" technique in terms of pain control and post-operative bleeding. It is however generally unpopular because of messy associated bleeding and consequent time delay. The embodiments of the present invention incorporate a beveled edge to allow meticulous blunt dissection simultaneously with accompanying electrocautery.

Suction

Suction at the tip of the cautery device allows rapid clearing of blood from the field and direct cautery application to the site of bleeding. Currently available suction tips are rounded and blunt making them inappropriate for rapid cutting of tissue. Introducing a bevel and angle to the suction tip corrects this problem. In one embodiment, no insulation is provided around the distal circumference of the tip which allows tissue contact with the full extent of the suction tube. The angle of the tip positions the suction hole directly parallel to the plane of the bleeding site. In particular, the angle is superbly oriented for cauterization of the superior pole vessels, which are prone to cause bleeding both intra-operatively and postoperatively. Intra-operative bleeding with this technique is virtually nil and thermal trauma is minimal.

In short, the embodiments of the present invention combine the advantages of suction electrocautery along with needle-tip electrocautery, while incorporating the advantage of the time-honored blunt dissection technique. This eliminates the need for two separate cautery devices to be opened for each case. Most importantly, it provides the surgeon with a tool to meticulously and atraumatically dissect tonsils in a true sub-capsular plane with a minimum of bleeding and thermal injury.

The proposed semi-conical tip is a natural shape for pushing open tissue borders in a tight space. Millimeters matter in confined regions. The proposed tip at its leading edge is sharp enough to allow precise pinpoint cutting.

One embodiment of the invention may comprise a suction cautery dissector comprising a handle assembly, a tubing assembly having a suction channel formed therein, the tubing assembly comprising a first portion connected to the handle assembly and a distal end, and a tip assembly at the distal end of the insulated tubing assembly, the tip assembly comprising a substantially co-planar, enclosed cautery surface with a beveled leading edge sharpened for dissecting tissue. The cautery surface may provide an opening formed therein that communicates with the suction channel in the insulated tubing assembly and being operably connected to an electrical source. The tip assembly may comprise a tip wall terminating at the cautery surface and wherein the tubing assembly comprises an insulating layer covering the suction channel from the first portion to the distal end, terminating at a minimum predetermined distance (e.g., 2 mm to 0.5 cm) along the tip wall from the cautery surface around the circumference of the tip assembly to enable the tip assembly to make surface contact around the entire tip wall.

In various iterations of this embodiment, the tubing assembly comprises an angled portion between the first portion and the distal end, the angled portion forming an obtuse angle (e.g., about 140 degrees) between the distal end and the first portion (e.g., about 2–4 cm from the leading edge of the tip assembly). The beveled leading edge may be beveled at an angle of approximately 45 degrees, although other angles may also be used as desired. In addition, in various iterations, the tip assembly and cautery surface may be operably connected to an electrical source through the suction channel, the suction channel comprising an electrically conducting material connected to an electrical wire in the handle assembly. The suction channel may also connect to a suction port in the handle assembly to control suction of air through the opening in the cautery surface. Overall, these various iterations and embodiments may yield a tool that provides a tip assembly that operates to simultaneously dissect tissue with the beveled leading edge, cauterize tissue with at least the cautery surface and a portion of the tip wall and remove materials by suction through the opening in the cautery surface.

Other advantages and objects of the present invention may be ascertained from a review of the drawings and detailed description that follows.

BRIEF DESCRIPTION OF THE DRAWINGS

FIG. 3 depicts a top view of a suction cautery dissector according to an embodiment of the present invention.

FIG. 4 depicts an exploded side view of a tip assembly of a suction cautery dissector according to an embodiment of the present invention.

FIG. 5 depicts a sectional view of a tip assembly according to an embodiment of the present invention.

FIG. 6 depicts an exploded side view of a tip of the prior art.

FIG. 7 depicts an exploded side view of a tip assembly according to an embodiment of the present invention.

FIG. 8 depicts an oblique, exploded side view of a tip of the prior art.

FIG. 9 depicts an oblique, exploded side view of a tip assembly according to an embodiment of the present invention.

FIG. 10 depicts another oblique, exploded side view of a tip assembly according to an embodiment of the present invention.

DETAILED DESCRIPTION OF EMBODIMENTS

Figure 1:
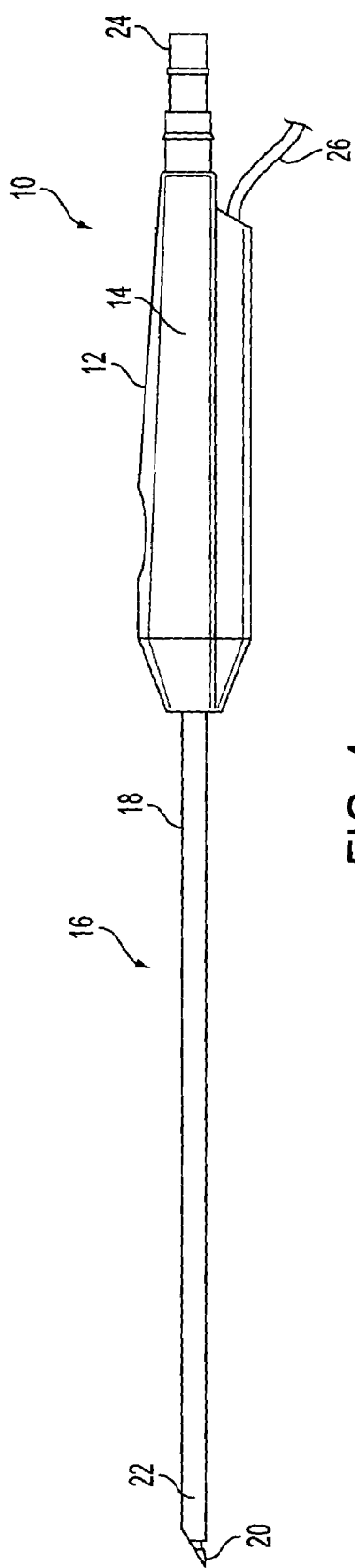
FIG. 1 depicts a public domain suction coagulator of the prior art.
Figure 2:
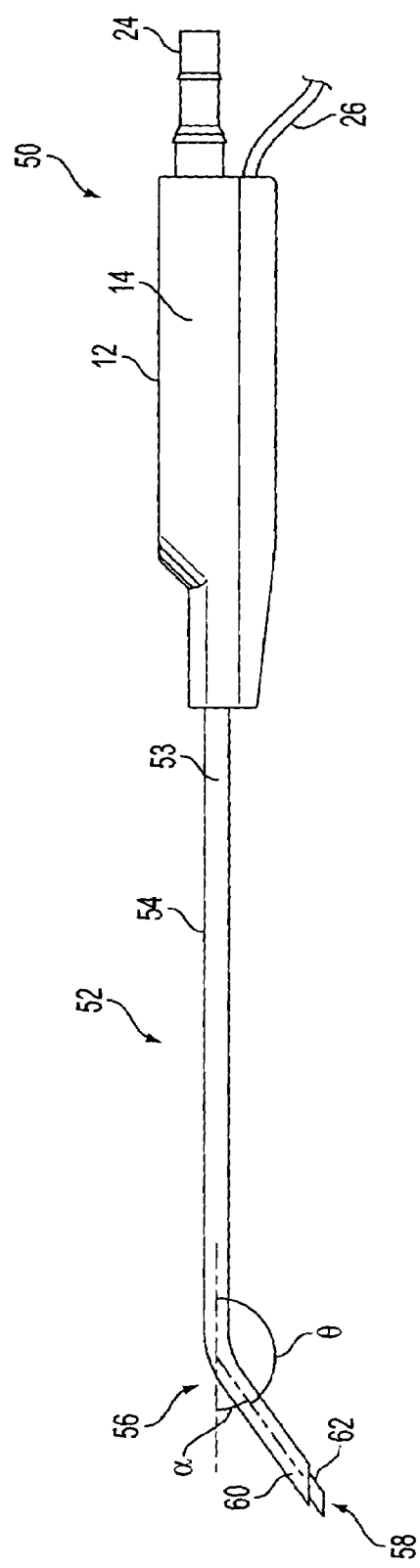
FIG. 2 depicts a side view of a suction cautery dissector according to one embodiment of the present invention.
Figure 12:
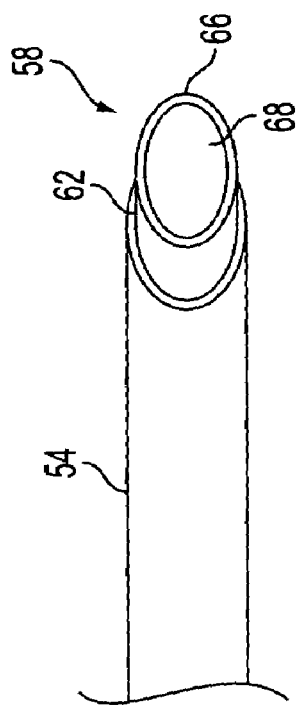
FIG. 12 depicts an exploded bottom view of a tip assembly according to an embodiment of the present invention.
Figure 14:
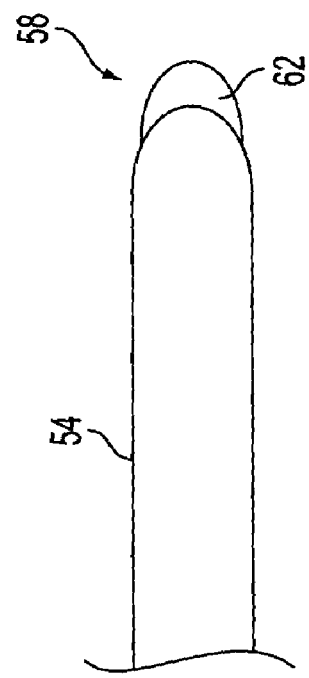
FIG. 14 depicts an exploded top view of a tip assembly according to an embodiment of the present invention.
Figure 11:
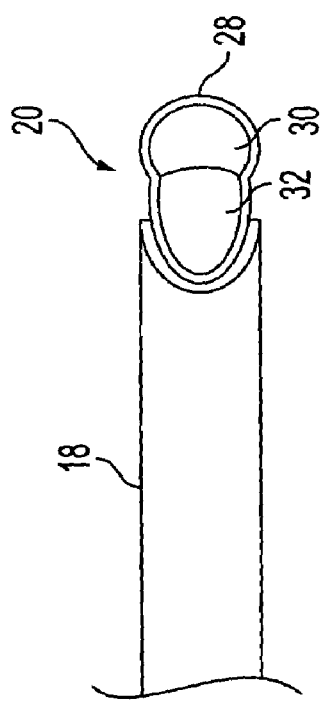
FIG. 11 depicts an exploded bottom view of a tip of the prior art.
Figure 13:
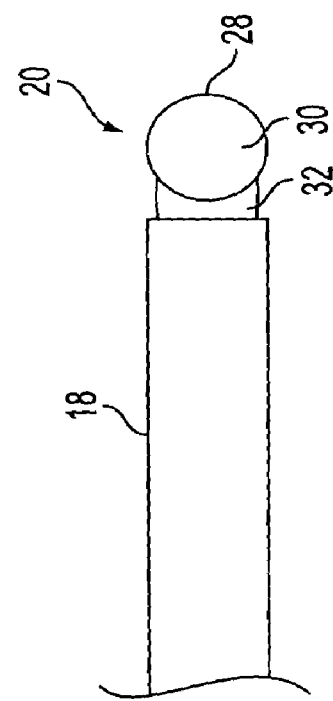
FIG. 13 depicts an exploded top view of a tip according to the prior art.
Figure 15:
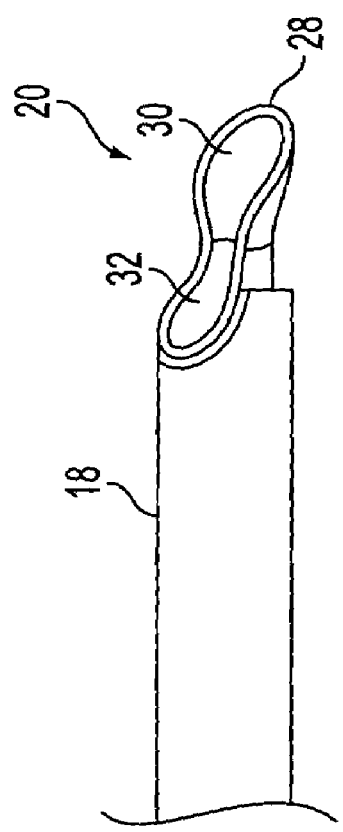
FIG. 15 depicts an oblique, exploded side view of a tip according to the prior art.
Figure 16:
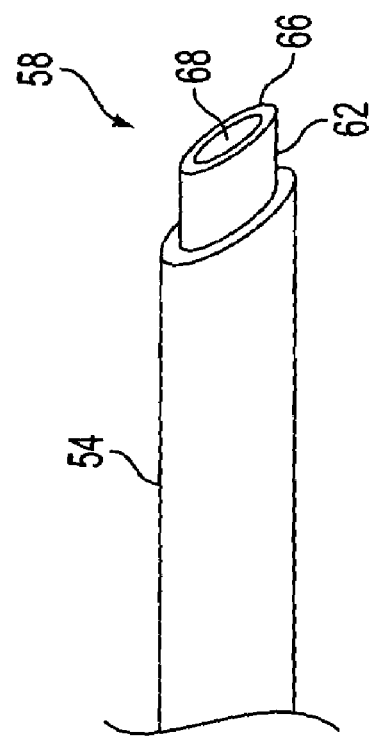
FIG. 16 depicts another exploded side view of a tip assembly according to an embodiment of the present invention.

As discussed above, various embodiments and iterations of the present invention relate to an improved suction cautery dissector as depicted, for example, in FIGS. 2, 3–5, 7, 9, 10, 12, 14, and 16. FIG. 2 depicts a suction cautery dissector 50 that provides a handle assembly 12 and an optional handle gripping mechanism 14. As depicted in FIG. 2, a groove or ridge may be provided for handle gripping mechanism 14. Also, any other similar structure may be used to enable the surgeon or other user to get a better grip on the handle of the device. This structure is optional or may be enhanced with additional such structures around the periphery of handle assembly 12. In addition, the shape and size of the handle assembly 12 may be modified to provide better gripping for the surgeon using the tool as will be appreciated by those of ordinary skill in the art.

Connected into handle assembly 12 may be provided an insulated metal tubing assembly 52. According to one embodiment, a metal tubing assembly 52 may continue into the interior of handle assembly 12 for functions described in detail below. Insulated metal tubing 52 may comprise a first portion 53 that adjoins handle assembly 12, an angled portion 56, and a tip assembly 58 located at a distal end 62 of the insulated metal tubing 52.

The first portion 53 may be connected into the interior of handle assembly 12 according to known technologies and methodologies for other similarly situated public domain devices. Indeed, the structure of handle assembly 12 may be as shown in public domain device 10 and other similar devices known to those of ordinary skill in the art. First portion 53 may be provided with a layer of electrical insulation 54 that extends around the periphery of first portion 53 continuously through angled portion 56 and to a point on tip assembly 58 as for example depicted in the figures. Insulation layer 54 may comprise known electrical insulation layers such as those utilized in public domain devices.

Angled portion 56 may be disposed at a point approximately 2 centimeters from the end of the tip of tip assembly 56, although other locations along the insulated metal tubing 52 may also be used according to known preferences. Additionally, insulated metal tubing 52 may be relatively malleable, enabling the surgeon or other user to modify the angle and location of angled portion 56 or to even implement multiple angled portions along tubing 52. According to one specific embodiment, the angled portion 56 may form an obtuse angle, $\theta$, as shown in FIG. 2, which may be provided to be 140 degrees thereby providing an angle, $\alpha$, with respect to the plane of the generally straight portion of approximately 40 degrees. Tip assembly 58 may be disposed at the distal end 60 of the insulated metal tubing 52. Tip assembly 58 may comprise a beveled metal tip 62 that does not have an insulation layer 58 disposed around its periphery. The details of beveled metal tip 62 may be better seen with reference to other figures described in detail below.

As shown in FIG. 3, which is a top view of suction cautery dissector 50, a finger vacuum port 64 may be disposed in the top of handle assembly 12 for use by a surgeon's thumb or finger in performing the procedures. Specifically, when the thumb of the surgeon covers the vacuum port 64, the vacuum pressure in the suction chamber draws air through the tip assembly 58 out through suction port 24 through the chamber disposed in insulated metal tubing 52 that connects to suction port 24. When the surgeon removes his or her thumb, air is drawn through finger vacuum port 64, reducing airflow and is not drawn through tip assembly 58. By locating the finger vacuum port on the top of the handle, the surgeon may be able to utilize his or her thumb for that procedure during the blunt dissection operation in which the tool is being moved in a direction along the device as shown in FIG. 3 with the tip assembly doing the cutting in that direction. Additionally, because of the angles of the tip assembly and the angled portion 56 in the preferred embodiment, the plane of the cutting surface and the plane of the handle assembly are substantially parallel although offset by maybe a few degrees. Thereby, the surgeon is able to move the tool in a plane directly outward from his or her body with the thumb covering the vacuum port as desired during the operation or procedure.

FIG. 4 depicts an exploded view of tip assembly 58 which comprises the distal end 60, beveled metal tip 62, beveled leading edge 66, and suction chamber 68. Specifically, beveled medal tip 62 may be provided in such an arrangement that the insulation layer 54 stops a minimum predetermined distance from the edge on the entire periphery of the tip to enable the entire beveled metal tip 62 to provide cauterization of tissue with which it comes into contact. Suction chamber 68 may comprise an opening in beveled metal tip 62 to provide beveled metal tip 62 with a cautery surface around the opening. The cautery surface may be best depicted in FIG. 7 as element 70. As shown in FIG. 5, beveled metal tip 62 may enclose in a circumferential manner suction chamber 68. In addition, the distance between the termination point of insulation layer 54 and the outer edge of leading edge 66 may comprise a distance, $l_2$, and the distance between the bottom portion of beveled metal tip 62 from a side angle and insulating layer 54 may comprise a distance, $l_1$. According to one embodiment, the distance $l_1$ and $l_2$ may be equal as is the distance between the metal edge and insulation layer 52 around the periphery. However, variations in the distances may also be provided so long as $l_1$ and $l_2$ exceed a minimum predetermined distance in the preferred arrangement. According to one embodiment, that minimum predetermined distance may comprise any distance from 2 mm to 0.5 centimeters, although other distances may also be used to the extent that a wall 72 of beveled metal tip 62 is sufficiently wide to provide cauterization.

FIGS. 7, 9, 10, 12, 14 and 16 depict various other views of the tip assembly 58 according to an embodiment of the present invention. As these views illustrate, the insulation layer 54 terminates at a point such that sufficient surface area on the wall of the tip assembly is provided for purposes of cauterizing as the tissue is being dissected by the beveled metal tip 62.

Various modifications may be made to the present design within the scope of the present invention. For example, whereas the shape of the cross section is depicted as circular or ovoid, other shapes may also be provided within the scope of the present invention, including elliptical shapes, trapezoidal shapes, or other shapes designed such that a cutting edge is provided and sufficient surface area is created for purposes of cauterizing tissue. Other improvements and modifications may be readily understood by those of ordinary skill in the art.

While the foregoing description includes details and specificities, it should be understood that such details and specificities have been included for the purposes of explanation only, and are not to be interpreted as limitations of the present invention. Many modifications to the embodiments described above can be made without departing from the spirit and scope of the invention, as it is intended to be encompassed by the following claims and their legal equivalents.

What is claimed is:

1. A suction cautery dissector comprising:
   a handle assembly;
   a tubing assembly having a suction channel formed therein, the tubing assembly comprising a first portion connected to the handle assembly and a distal end;
   a tip assembly at the distal end of the tubing assembly, the tip assembly comprising a cautery surface with a beveled leading edge sharpened for dissecting tissue and a tip wall terminating at the cautery surface, the cautery surface having an opening formed therein that communicates with the suction channel in the tubing assembly and being operably connected to an electrical source, the cautery surface comprising a cauterizing plane;
   wherein the tubing assembly comprises an insulating layer covering the suction channel from the first portion to the distal end, terminating at a minimum predetermined distance along the tip wall from the cautery surface around the circumference of the tip assembly to enable the tip assembly to make surface contact around the entire tip wall, the insulating layer terminating at a substantially co-planar insulation termination plane; and
   wherein the cauterizing plane and the insulation termination plane are substantially parallel.

2. The suction cautery dissector of claim 1 wherein the tubing assembly comprises an angled portion between the first portion and the distal end, the angled portion forming an obtuse angle between the distal end and the first portion.

3. The suction cautery dissector of claim 1 wherein the obtuse angle comprises approximately 140 degrees.

4. The suction cautery dissector of claim 1 wherein the vertex of the obtuse angle is positioned approximately 2 c.m. from the leading edge of the tip assembly.

5. The suction cautery dissector of claim 1 wherein the beveled leading edge is beveled at an angle of approximately 45 degrees.

6. The suction cautery dissector of claim 1 wherein the tip assembly and cautery surface are operably connected to an electrical source through the suction channel, the suction channel comprising an electrically conducting material connected to an electrical wire in the handle assembly.

7. The suction cautery dissector of claim 1 wherein the suction channel also connects to a suction port in the handle assembly to control suction of air through the opening in the cautery surface.

8. The suction cautery dissector of claim 1 wherein the tip assembly operates to simultaneously dissect tissue with the beveled leading edge, cauterize tissue with at least the cautery surface and a portion of the tip wall and remove materials by suction through the opening in the cautery surface.

9. The suction cautery dissector of claim 1 wherein the cautery surface comprises a semi-cylindrical shape.

10. The suction cautery dissector of claim 1 wherein the cautery surface is substantially co-planar.

11. The suction cautery dissector of claim 1 wherein the leading edge comprises an ovoid shape.

* * * * *